(12) United States Patent
Schumaier

(10) Patent No.: US 11,167,052 B2
(45) Date of Patent: Nov. 9, 2021

(54) ULTRAVIOLET LIGHT SANITIZER

(71) Applicant: Daniel R. Schumaier, Elizabethton, TN (US)

(72) Inventor: Daniel R. Schumaier, Elizabethton, TN (US)

( * ) Notice: Subject to any disclaimer, the term of this patent is extended or adjusted under 35 U.S.C. 154(b) by 22 days.

(21) Appl. No.: 16/887,309

(22) Filed: May 29, 2020

(65) Prior Publication Data
US 2021/0308295 A1    Oct. 7, 2021

Related U.S. Application Data

(60) Provisional application No. 63/006,223, filed on Apr. 7, 2020.

(51) Int. Cl.
*A61L 2/10* (2006.01)
*B08B 7/00* (2006.01)

(52) U.S. Cl.
CPC .............. *A61L 2/10* (2013.01); *B08B 7/0057* (2013.01); *A61L 2202/11* (2013.01); *A61L 2202/20* (2013.01)

(58) Field of Classification Search
CPC .... A61L 2/10; A61L 2202/11; A61L 2202/20; B08B 7/0057
USPC ............................ 250/453.11, 454.11, 455.11
See application file for complete search history.

(56) References Cited

U.S. PATENT DOCUMENTS

| | | |
|---|---|---|
| 5,404,105 A | 4/1995 | Chari |
| 5,640,783 A | 6/1997 | Schumaier |
| 5,852,879 A | 12/1998 | Schumaier |
| D414,304 S | 9/1999 | Schumaier |
| D467,394 S | 12/2002 | Schumaier |
| 7,062,057 B2 | 6/2006 | Wu |
| D536,491 S | 2/2007 | Schumaier |
| 7,182,820 B2 | 2/2007 | Campbell et al. |
| 8,112,900 B2 | 2/2012 | Romanek |
| 8,597,588 B1 * | 12/2013 | Trabalka ................... A61L 2/10 422/300 |
| 9,843,870 B2 | 12/2017 | Naumann |
| 10,328,166 B2 | 6/2019 | Georgeson |
| 10,932,513 B1 * | 3/2021 | Day ....................... A42B 1/244 |
| 2004/0073275 A1 | 4/2004 | Maltan et al. |

(Continued)

FOREIGN PATENT DOCUMENTS

| | | |
|---|---|---|
| CN | 201018665 | 2/2008 |
| CN | 103747388 A | 4/2014 |

(Continued)

*Primary Examiner* — Nicole M Ippolito
(74) *Attorney, Agent, or Firm* — Luedeka Neely Group, P.C.

(57) ABSTRACT

A sanitizing apparatus sanitizes headsets or eyeglasses between uses by patients. The apparatus includes a UV-C lamp that generates UV-C light at a proper frequency and intensity during a time period of sufficient duration to kill bacterial and viral infectants on surfaces of the headsets or eyeglass frames that may come in contact with a patient's skin. The apparatus may also be used for sanitizing bone vibrators, otoacoustic emissions testing equipment, headsets used in impedance testing, insert earphones, and response buttons that are commonly used in audiometric testing. The apparatus can also be used in communication situations in which headsets are utilized with microphones, such as in call centers.

20 Claims, 5 Drawing Sheets

(56) References Cited

U.S. PATENT DOCUMENTS

| | | |
|---|---|---|
| 2006/0220620 A1 | 10/2006 | Aradachi et al. |
| 2009/0296968 A1 | 12/2009 | Wu et al. |
| 2010/0088916 A1 | 4/2010 | Romanek |
| 2012/0216418 A1 | 8/2012 | Serman et al. |
| 2015/0162770 A1 | 6/2015 | Choi et al. |
| 2016/0165367 A1 | 6/2016 | Ochsenbein |
| 2016/0277848 A1 | 9/2016 | Naumann |
| 2016/0301287 A1 | 10/2016 | Nagata et al. |
| 2017/0319725 A1* | 11/2017 | Hann ................. A61L 2/24 |
| 2017/0333618 A1* | 11/2017 | Krohn ............... A61M 5/001 |
| 2018/0123355 A1 | 5/2018 | Olson et al. |
| 2018/0123367 A1 | 5/2018 | Higgins et al. |
| 2019/0208342 A1 | 7/2019 | Higgins et al. |
| 2021/0187819 A1* | 6/2021 | Connell ............... B29C 51/02 |

FOREIGN PATENT DOCUMENTS

| | | |
|---|---|---|
| CN | 104534822 A | 4/2015 |
| CN | 205901402 U | 1/2017 |
| DE | 202017107151 U1 | 1/2018 |
| KR | 20120085980 A | 8/2012 |
| WO | 2007066908 A1 | 6/2007 |
| WO | 2019241759 A1 | 12/2019 |

\* cited by examiner

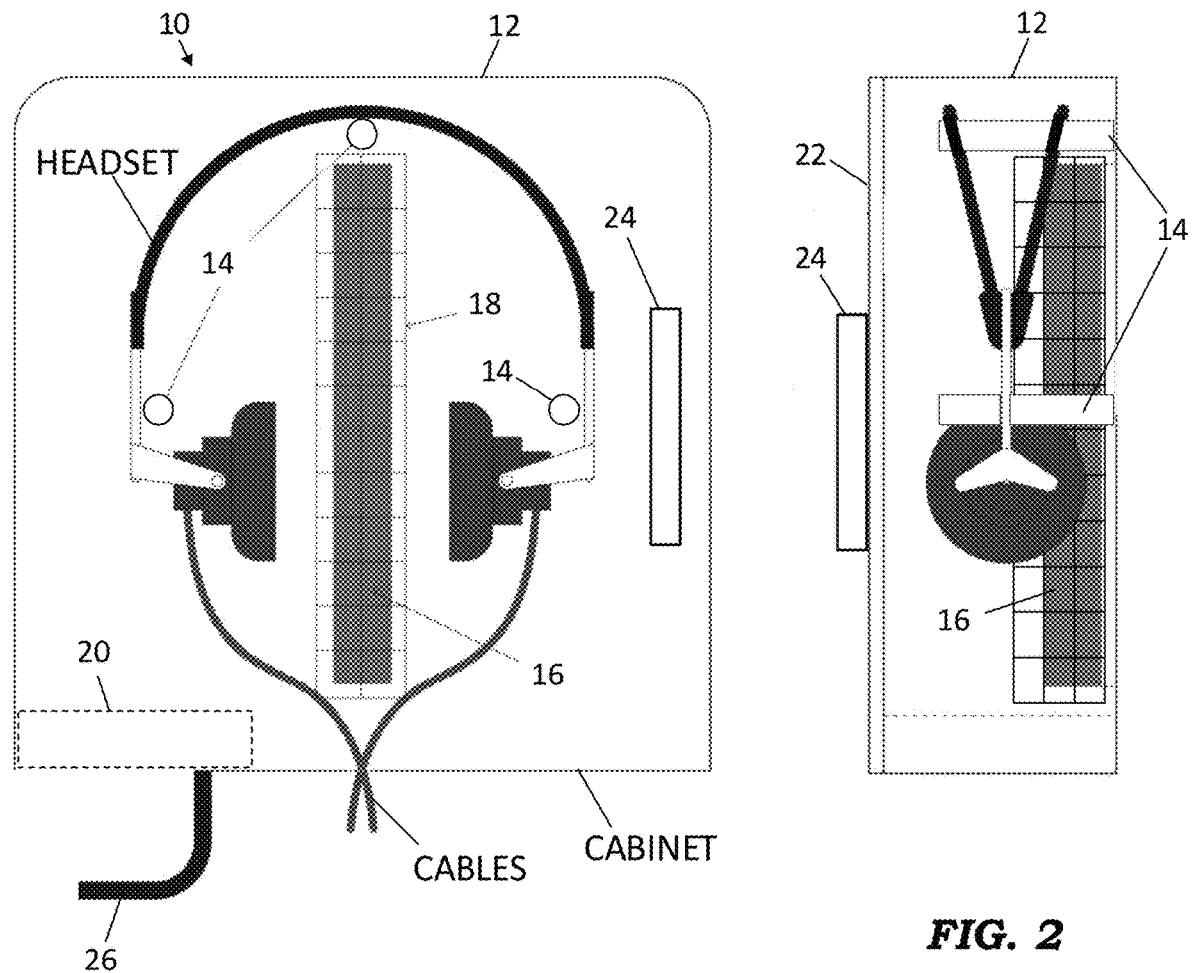
FIG. 1
FIG. 2
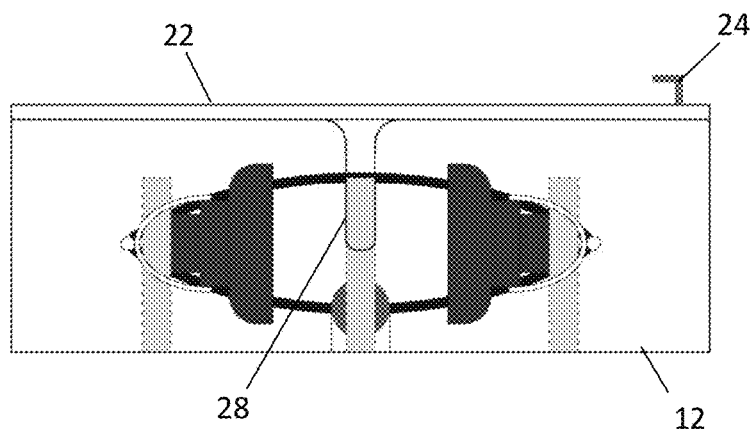
FIG. 3

ULTRAVIOLET LIGHT SANITIZER

RELATED APPLICATIONS

This application claims priority to provisional patent application Ser. No. 63/006,223, filed Apr. 7, 2020, titled "Headset Sanitizer," the entire contents of which are incorporated herein by reference.

FIELD

This invention relates to the field of sanitization of auditory and optical items worn on a person's head. More particularly, this invention relates to an apparatus for sanitizing headsets used in auditory testing and eyeglasses used in optical fitting sessions.

BACKGROUND

Audio headsets are often used when an audiologist conducts tests to evaluate hearing impairment of patients. Typically, a single headset is used sequentially on multiple patients. To maintain proper hygiene, the headset should be wiped down with a disinfectant wipe or otherwise cleaned between uses to kill bacterial or viral infectants. Such wet cleaning methods are time consuming and can cause damage to circuitry within the headset after multiple cleanings due to entry of liquid disinfectant solutions into openings in the earphone portions of the headset.

Also, when opticians fit glasses, it often involves the patient trying on several sets of frames. Considering the potential danger of viral contaminates, there is a need to sanitize the frames between fitting sessions.

What is needed, therefore, is an apparatus that disinfects headsets between uses in a manner that is a less manually intensive, less time consuming, and less harmful to the headsets. The desired apparatus should thoroughly disinfect the entire headset, including the cushions, earphones, head strap, and cable. Such an apparatus is also needed for disinfection of multiple sets of eyeglass frames between fittings.

SUMMARY

The above and other needs are met by embodiments of a sanitizing apparatus that sanitizes headsets or eyeglasses between uses by patients. In the various embodiments, the apparatus includes a UV-C lamp that generates UV-C light at a proper frequency and intensity during a time period of sufficient duration to kill bacterial and viral infectants on surfaces of the headsets or eyeglass frames that may come in contact with a patient's skin.

In various embodiments, the apparatus may also be used for sanitizing bone vibrators, otoacoustic emissions testing equipment, headsets used in impedance testing, insert earphones, and response buttons that are commonly used in audiometric testing. The apparatus can also be used in communication situations in which headsets with microphones are utilized, such as in call centers, or in entertainment or gaming situations in which virtual reality goggles/headsets are utilized.

One preferred embodiment is directed to a sanitizing apparatus for sanitizing a headset having a cable that is connected to hearing test equipment. The sanitizing apparatus includes a cabinet having an interior space and a door that moves between an open position and a closed position. A UV-C light source is disposed within the interior space of the cabinet for generating UV-C light. Means are included for suspending the headset within the cabinet in a position in which the headset is illuminated by the UV-C light. The cabinet includes an opening through which the cable may pass from inside to outside the cabinet when the headset is suspended within and the door of the cabinet is closed. When the door of the cabinet is open, the opening allows insertion of the cable into and removal of the cable from the opening without disconnecting the cable from the hearing test equipment disposed outside the cabinet.

In some embodiments, the means for suspending the headset within the cabinet include a central peg disposed above the UV-C light source and a pair of pegs disposed to either side of the UV-C light source. When the headset is suspended from the central peg, the pair of pegs hold the earphone portions of the headset outward from the UV-C light source in a position in which interiors of the earphone portions are illuminated by the UV-C light.

In some embodiments, the positions of the pegs may be adjusted to accommodate headsets of various sizes.

In some embodiments, the sanitizing apparatus includes a door sensor for generating a signal that indicates whether the door is in the open position or the closed position.

In some embodiments, the sanitizing apparatus includes a headset sensor for generating a signal that indicates whether a headset is present in the cabinet.

In some embodiments, the sanitizing apparatus includes timer circuitry for timing a period during which the UV-C light source is activated to illuminate the headset.

In some embodiments, the inside surfaces of the cabinet are UV-C reflective.

In some embodiments, the sanitizing apparatus includes circuitry to determine that the UV-C light source needs to be replaced, and to provide a visual or auditory signal to indicate when it is time for replacement.

In some embodiments, the sanitizing apparatus includes a timer for determining a cumulative time during which the UV-C light source has been activated since a previous replacement of the UV-C light source.

In another aspect, an embodiment is directed to an apparatus for sanitizing multiple pairs of eyeglasses. The sanitizing apparatus includes a cabinet having an interior space and a door that is movable between an open position and a closed position. A UV-C light source is disposed within the interior space of the cabinet for generating UV-C light. One or more rack units are removably disposed within the interior of the cabinet. Each rack unit includes multiple wire shelves. Each wire shelf is configured to hold one or more of the pairs of eyeglasses.

In some embodiments, the UV-C light source is generally vertically disposed at a horizontal center of the interior space of the cabinet. The rack units of these embodiments include a first rack unit that is horizontally offset to the right side of the UV-C light source, and a second rack unit that is horizontally offset to the left side of the UV-C light source.

In some embodiments, the rack units are rotatable about their vertical axes, and the sanitizing apparatus includes one or more motor units for causing the rack units to rotate about their vertical axes.

In some embodiments, the sanitizing apparatus includes a door sensor for generating a signal that indicates whether the door is in the open position or the closed position.

In some embodiments, the sanitizing apparatus includes one or more sensors for generating one or more signals that indicate whether the one or more rack units are present in the cabinet.

In some embodiments, the sanitizing apparatus includes timer circuitry for timing a period during which the UV-C light source is activated to illuminate the one or more pairs of eyeglasses.

In another aspect, a headset sanitizer includes a cabinet having an interior space and a UV-C light source disposed therein for generating UV-C light. Within the cabinet is central peg from which a headset may be suspended in a position in which the headset is illuminated by the UV-C light. A pair of pegs, including one peg disposed to either side of the UV-C light source, hold the earphone portions of the headset outward from the UV-C light source in a position in which interiors of the earphone portions are illuminated by the UV-C light. The positions of the pegs are adjustable to accommodate headsets of various sizes.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein:

FIG. 1 depicts a front view of a headset sanitizer according to a first embodiment;

FIG. 2 depicts a side view of a headset sanitizer according to the first embodiment;

FIG. 3 depicts a bottom view of a headset sanitizer according to the first embodiment;

DETAILED DESCRIPTION

Figure 4:
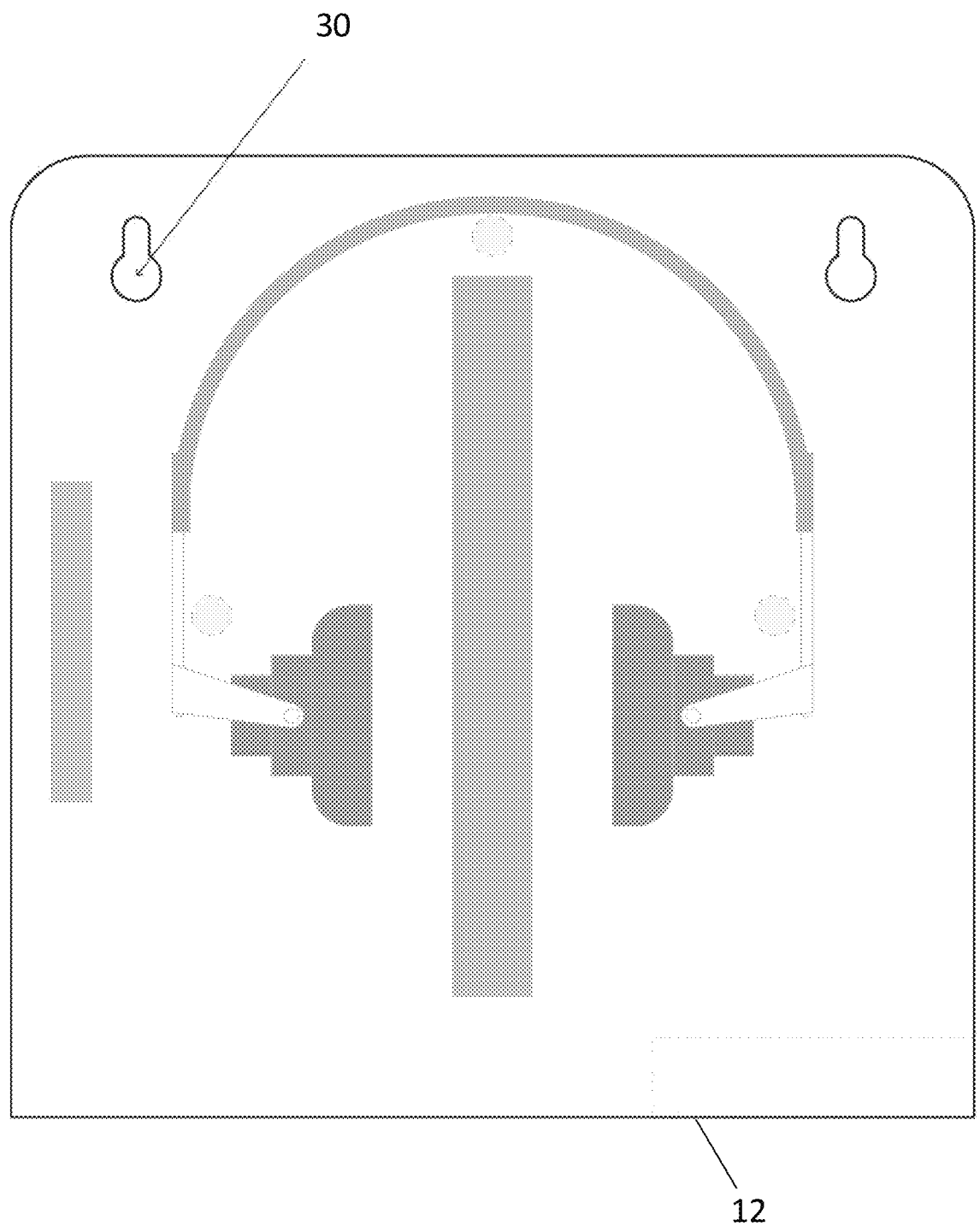
FIG. 4 depicts a rear view of a headset sanitizer according to the first embodiment.

As shown in FIGS. 1-4, a first embodiment of a ultraviolet light sanitizing apparatus 10 includes a cabinet 12 that can be attached on a wall in a vertical orientation using a pair of mounting holes 30 in its rear surface (FIG. 4). Centrally disposed within the cabinet 12 is an ultraviolet (UV-C) lamp 16. In a preferred embodiment, the UV-C lamp 16 generates germicidal radiation in the UV-C range (250-270 nm wavelength) which is known to be lethal to microorganisms given sufficient intensity and exposure time. The UV-C lamp 16 is preferably disposed within a protective cage 18 attached to the inner surface of the rear wall of the cabinet 12. In a preferred embodiment, the exterior dimensions of the cabinet are 12 inches wide by 12 inches high by 4 inches deep.

Three pegs 14 are also attached to the rear inner surface and extend outward therefrom into the interior of the cabinet 12. One of the pegs 14 is disposed directly above the UV-C lamp 16 and the other two are disposed to either side of the lamp. In the embodiment of FIG. 1, a headset to be sanitized is hung by its strap from the upper central peg 14 and the strap portions of the headset supporting the earphones are disposed to the outside of the two side pegs 14. In this manner, the earphones are separated from each other and their interior portions are positioned to either side of the UV-C lamp to enhance illumination. In one embodiment, the pegs 14 are molded from plastic or metal and are about 3.5 inches in length and about ½ inch in diameter.

Figure 6B:
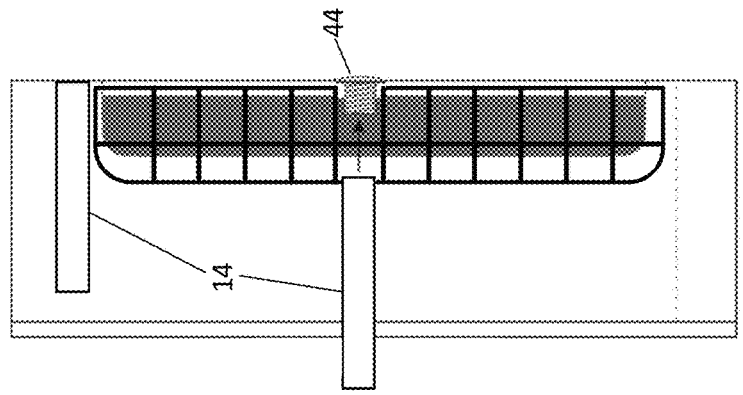
FIGS. 6A, 6B, and 6C depict a headset sanitizer that accommodates different sizes and types of headsets according to a second embodiment.
Figure 6A:
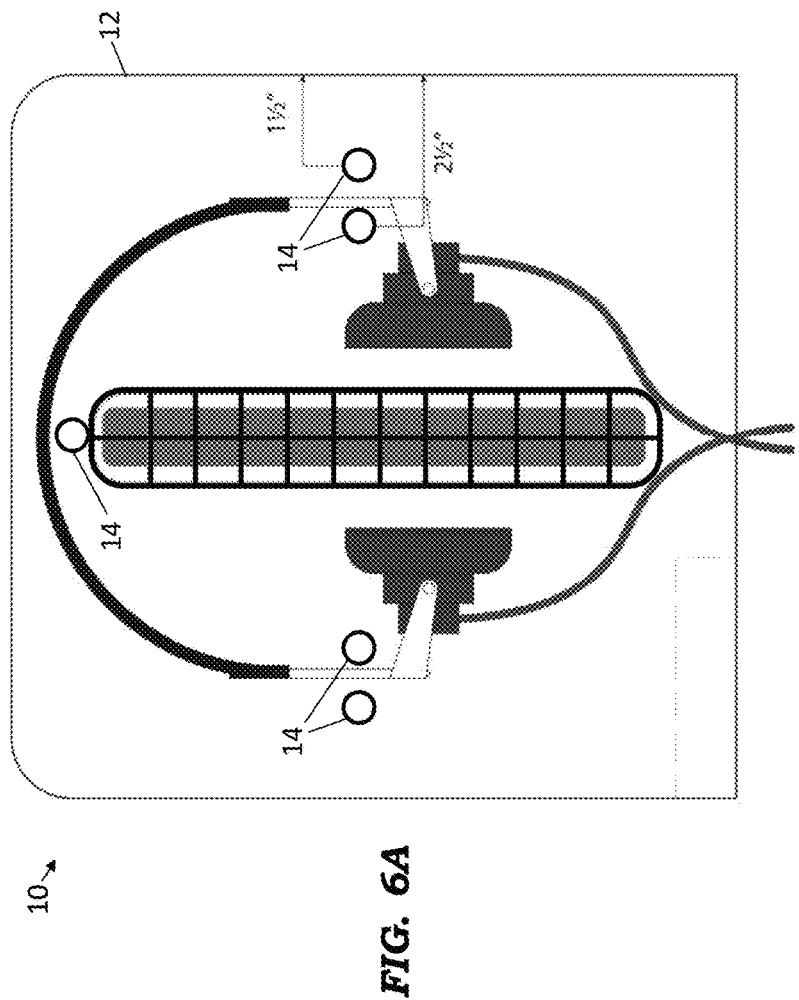
Figure 6C:
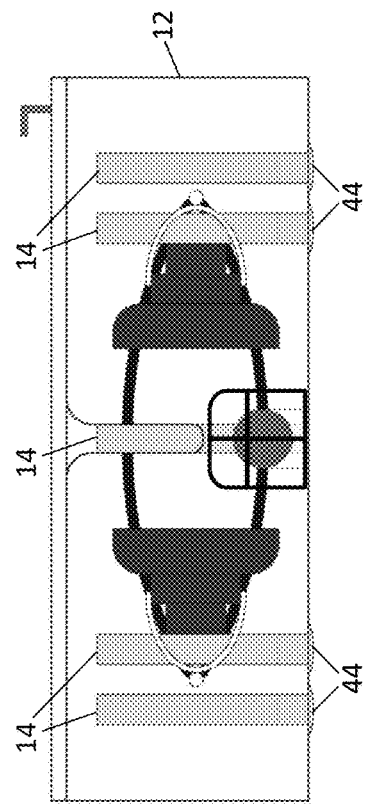

In a second embodiment depicted in FIGS. 6A, 6B, and 6C, the side pegs 14 comprise interior threaded rods that receive bolts 44 extending through the rear wall of the cabinet 12, and multiple sets of holes for the bolts 44 are provided at various spacings. In this way, the side pegs 14 may be removed and placed at the other locations to provide different spacings with respect to the UV-C lamp. This allows the spacing between the earphone portions of the headset to be adjusted appropriately depending on the type of headset and size of earphone.

Figure 5:
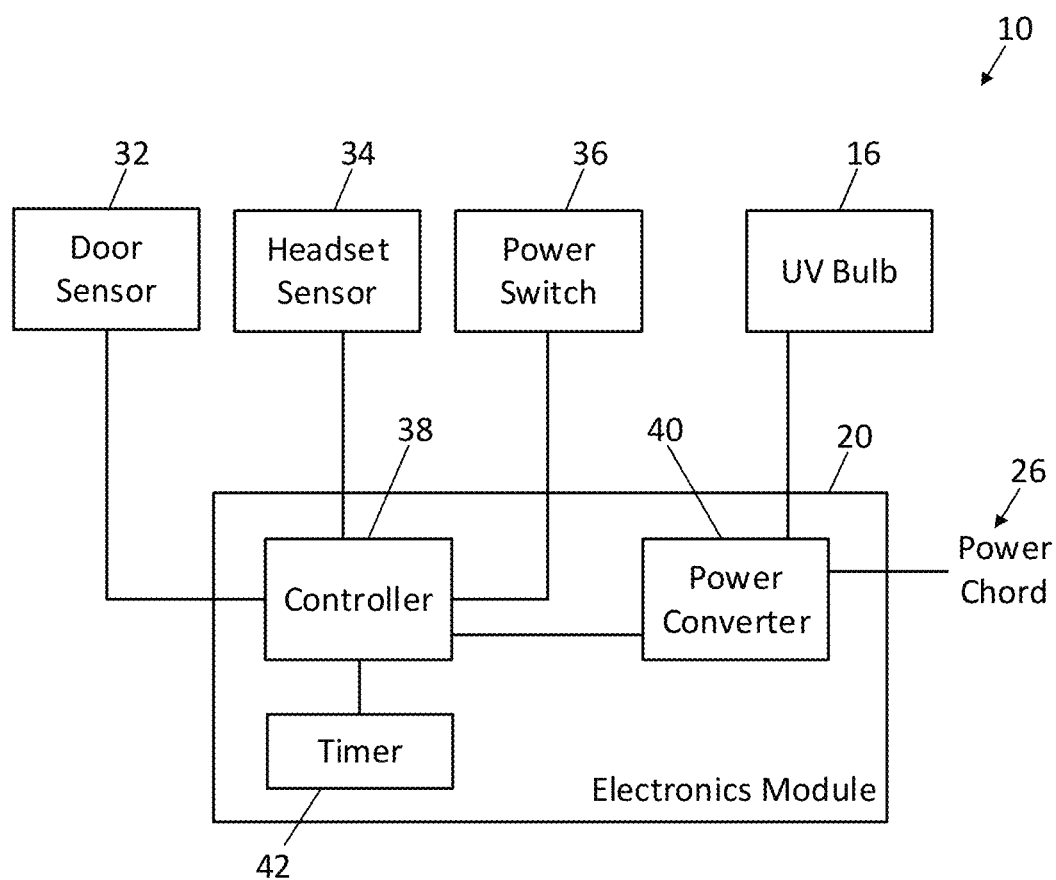
FIG. 5 depicts an electrical block diagram of a headset sanitizer according to an embodiment.

All of the various embodiments of the apparatus 10 preferably include an electronics module 20 disposed within the bottom portion of the cabinet 12. As depicted in FIG. 5, the electronics module 20 preferably includes a controller 38 that receives signals from a timer 42, a door sensor 32, a headset sensor 34, and a power switch 36. The door sensor 32 preferably comprises a proximity switch or other sensor positioned adjacent the cabinet door 22 to sense the state of the cabinet door 22 as being open or closed. The headset sensor 34 preferably comprises a proximity switch or other sensor positioned on or adjacent the central peg 14 to sense whether a headset is present in the cabinet. In a preferred embodiment, the controller 38 also counts the number of times the UV-C lamp 16 has been activated, and the length of time it has been on. When the performance of the lamp 16 degrades, an auditory or visual signal will let the user know the lamp 16 needs to be changed. The electronics module 20 also preferably includes power converter circuitry 40 to convert the standard voltage from the power cord 26 to the voltage needed to power the UV-C lamp 16.

Based on the door sensor 32 sensing that the door state has changed from open to closed, and the headset sensor 34 sensing that a headset is present in the cabinet 12, the controller 38 causes the UV-C lamp 16 to be powered on and the timer circuitry 42 to be activated to begin timing a sanitization period. In one embodiment, a sanitization period of 60 seconds is sufficient to thoroughly sanitize the headset, although this period may be longer or shorter in other embodiments depending on the illumination intensity of the UV-C lamp 16. At the completion of the sanitization period, the timer circuitry 42 automatically turns off the UV-C lamp 16. Also, if the cabinet door is opened before the completion of the sanitization period, the UV-C lamp 16 is automatically turned off to protect personnel from exposure to the UV-C light.

Because a preferred embodiment of the sanitizing apparatus 10 is for use in sanitizing a headset between uses by different patients, the cabinet 12 of the apparatus 10 is designed to be installed in a sound room in which hearing tests are conducted. It is also configured to accommodate placement of the headset into the cabinet 12 without having to disconnect the headset from the testing equipment. Accordingly, the cabinet 12 includes a cable slot 28 in the bottom wall of cabinet 12, preferably directly below the UV-C bulb 16 as depicted in FIG. 3, through which the headset cable(s) can pass through the bottom wall while the door 22 is closed. In alternative embodiments, the apparatus 10 may be placed on a table utilizing a cabinet stand. A carrying handle also may be attached to the top of the cabinet 12. This configuration may be used in schools or where hearing screening is performed in different locations.

In a preferred embodiment, the power switch 36 controls activation of the sanitizing apparatus 10, which may be a capacitive touch switch for easy use and reduction of switch failure.

In a preferred embodiment, the interior surfaces of the cabinet 12 are UV-C reflective to maximize the illumination of the headset from various angles.

In a preferred embodiment, the apparatus 10 is powered by a 24V power source for safety purposes. In alternative embodiments, the apparatus 10 is powered by a 12V power source or is battery powered.

Figures 7A, 7B:
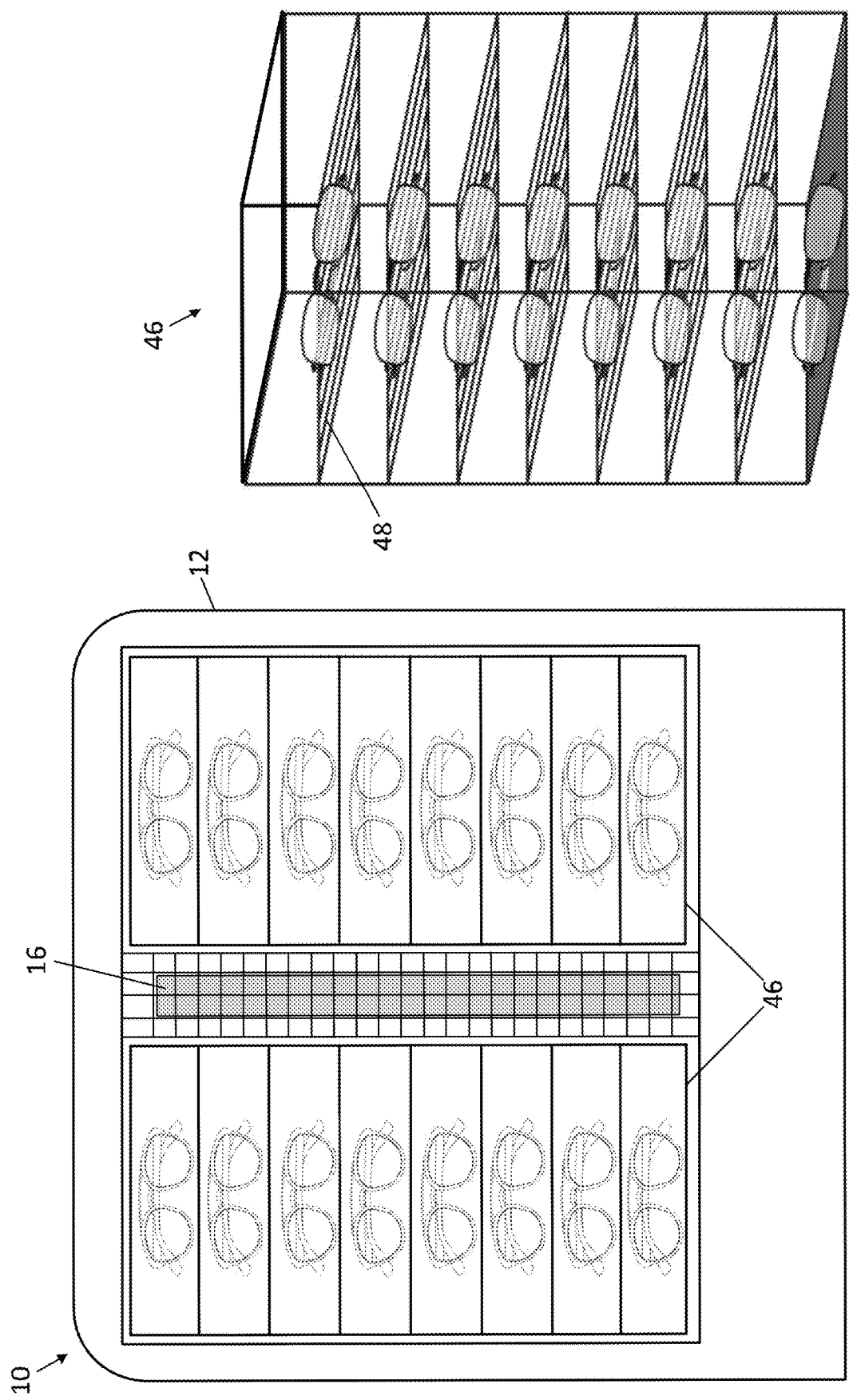
FIG. 7A depicts a front view of an eyeglasses sanitizer according to a third embodiment.
FIG. 7B depicts a perspective view of a wire rack for an eyeglasses sanitizer according to the third embodiment.

In a third embodiment depicted in FIGS. 7A and 7B, the sanitizing apparatus 10 is used for sanitizing eyeglasses. This embodiment may find use in an optician's shop to sanitize frames that a patient tried on during a fitting session. The eyeglasses to be sanitized are preferably placed on wire shelves 48 within removeable rack units 46. The wire shelves allow UV-C light from the lamp 16 to more completely illuminate all surfaces of the eyeglasses, taking advantage of the UV-reflective inner walls of the cabinet 12.

The functionality of the electronics module 20 and other circuitry of the third embodiment is substantially the same as that depicted in FIG. 5 and described above, except that instead of a headset sensor, the electronics provided in the third embodiment preferably includes one or more rack unit sensors to sense the presence of the rack units 46 within the cabinet 12.

In one embodiment of the eyeglasses sanitizer, each of the rack units 46 is rotatable about its central vertical axis within the cabinet 12, and one or more motors are provided in the lower portion of the cabinet 12 to rotate the rack units 46. Rotation of the rack units 46 during the sanitization cycle provides for better exposure of all surfaces of the eyeglasses to the UV-C light. In this embodiment, the wire shelves 48 are preferably circular, and the rack units 46 are generally cylindrical in shape.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A sanitizing apparatus for sanitizing a headset having a cable that connects the headset to hearing test equipment, the sanitizing apparatus comprising:
   a cabinet having an interior space and a door, wherein the door is movable between an open position and a closed position;
   a UV-C light source disposed within the interior space of the cabinet, the UV-C light source for generating UV-C light;
   means for suspending the headset within the interior space of the cabinet in a position in which the headset is illuminated by the UV-C light; and
   an opening in the cabinet through which the cable may pass from the interior space to outside the cabinet when the headset is suspended within the cabinet and the door of the cabinet is in the closed position,
   wherein, with the door of the cabinet in the open position, the opening allows insertion of the cable into the opening and removal of the cable from the opening without disconnecting the cable from the hearing test equipment disposed outside the cabinet.

2. The sanitizing apparatus of claim 1 wherein the means for suspending the headset within the cabinet comprise:
   a central peg disposed above the UV-C light source, wherein the headset is suspended from the central peg; and
   a pair of pegs comprising a peg disposed to either side of the UV-C light source for holding earphone portions of the headset outward from the UV-C light source in positions in which interiors of the earphone portions are illuminated by the UV-C light.

3. The sanitizing apparatus of claim 1 wherein positions of the pair of pegs may be adjusted to accommodate headsets of various sizes.

4. The sanitizing apparatus of claim 1 further comprising a door sensor for generating a signal indicative of whether the door is in the open position or the closed position.

5. The sanitizing apparatus of claim 1 further comprising a headset sensor for generating a signal indicative of whether a headset is present in the cabinet.

6. The sanitizing apparatus of claim 1 further comprising timer circuitry for timing a period during which the UV-C light source is activated to illuminate the headset.

7. The sanitizing apparatus of claim 1 wherein inside surfaces of the cabinet are UV-reflective.

8. The sanitizing apparatus of claim 1 further comprising circuitry to determine that the UV-C light source needs to be replaced, and to provide a visual or auditory signal to indicate that replacement is needed.

9. The sanitizing apparatus of claim 1 further comprising a timer for determining a cumulative time during which the UV-C light source has been activated since a previous replacement of the UV-C light source.

10. A sanitizing apparatus for sanitizing a plurality of pairs of eyeglasses, the sanitizing apparatus comprising:
    a cabinet having an interior space and a door, wherein the door is movable between an open position and a closed position;
    a UV-C light source disposed within the interior space of the cabinet, the UV-C light source for generating UV-C light; and
    one or more rack units that are removably disposed within the interior space of the cabinet, each of the one or more rack units comprising a plurality of wire shelves, wherein each of the wire shelves is configured for holding one or more of the to pairs of eyeglasses.

11. The sanitizing apparatus of claim 10 wherein:
    the UV-C light source is generally vertically disposed within the interior space of the cabinet; and
    the one or more rack units comprise a first rack unit horizontally offset to a right side of the UV-C light source and a second rack unit horizontally offset to a left side of the UV-C light source.

12. The sanitizing apparatus of claim 11 wherein the first and second rack units are rotatable about their vertical axes.

13. The sanitizing apparatus of claim 12 further comprising one or more motor units for causing the first and second rack units to rotate about their vertical axes.

14. The sanitizing apparatus of claim 10 further comprising a door sensor for generating a signal indicative of whether the door is in the open position or the closed position.

15. The sanitizing apparatus of claim 10 further comprising one or more sensors for generating one or more signals indicative of whether the one or more rack units are present in the cabinet.

16. The sanitizing apparatus of claim 10 further comprising timer circuitry for timing a period during which the UV-C light source is activated to illuminate the eyeglasses.

17. The sanitizing apparatus of claim 10 wherein inside surfaces of the cabinet are UV-reflective.

18. A headset sanitizer comprising:
a cabinet having an interior space;
a UV-C light source disposed within the interior space of the cabinet, the UV-C light source for generating UV-C light;
a central peg from which a headset may be suspended within the interior space of the cabinet in a position in which the headset is illuminated by the UV-C light; and
a pair of pegs comprising a peg disposed to either side of the UV-C light source for holding earphone portions of the headset outward from the UV-C light source in positions in which interiors of the earphone portions are illuminated by the UV-C light,
wherein positions of the pair of pegs may be adjusted to accommodate headsets of various sizes.

19. The headset sanitizer of claim 18 further comprising a sensor for generating a signal indicative of whether a headset is present in the cabinet.

20. The headset sanitizer of claim 18 further comprising timer circuitry for timing a period during which the UV-C light source is activated to illuminate the headset.

* * * * *